US00PP16595P2

(12) United States Plant Patent
Hanes

(10) Patent No.: US PP16,595 P2
(45) Date of Patent: May 30, 2006

(54) ***PELARGONIUM* PLANT NAMED 'CLIPS DARED'**

(50) Latin Name: *Pelargonium×hortorum*
Varietal Denomination: Clips Dared

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 122 days.

(21) Appl. No.: 11/094,749

(22) Filed: Mar. 31, 2005

(51) Int. Cl.
*A01H 5/00* (2006.01)

(52) U.S. Cl. ..... Plt./330

(58) Field of Classification Search ..... Plt./330
See application file for complete search history.

(56) References Cited

U.S. PATENT DOCUMENTS

PP15,513 P2 * 2/2005 Utecht ..... Plt./330

OTHER PUBLICATIONS

UPOV ROM GTITM Computer Database, GTI Jouve Retrieval Software 2005/03 Citation for 'Clips Dared'.*

* cited by examiner

*Primary Examiner*—Kent L. Bell
*Assistant Examiner*—W. C. Haas
(74) *Attorney, Agent, or Firm*—Jondle & Associates P.C.

(57) ABSTRACT

A *Pelargonium* cultivar particularly distinguished by its dark red flower color, dark green leaves, and vigorous growth habit is disclosed.

1 Drawing Sheet

Figure 1:
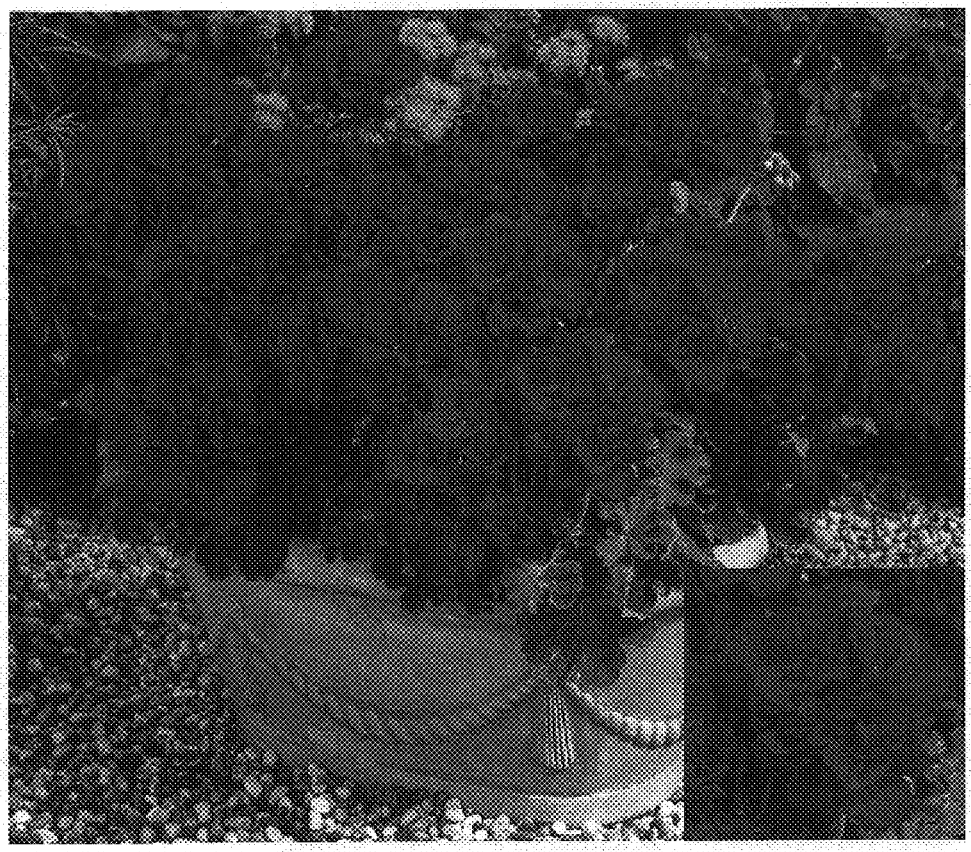

Genus and species: *Pelargonium×hortorum* L. H. Bailey.
Variety denomination: 'Clips Dared'.

BACKGROUND OF THE NEW PLANT

The present invention comprises a new and distinct cultivar of *Pelargonium,* botanically known as *Pelargonium× hortorum* L. H. Bailey, and hereinafter referred to by the cultivar name 'Clips Dared'. The new cultivar was propagated from a single seedling resulting from the open pollination of 8691-2, a red-flowered, unnamed, unpatented proprietary *Pelargonium* line and an unknown, proprietary, unpatented *Pelargonium* line.

The new cultivar was created in 2000 in Gilroy, Calif. and has been asexually reproduced repeatedly by vegetative cuttings in Gilroy, Calif. over a four year period. It has also been trialed at Gilroy, Calif., Litchfield, Mich., and Andijk, The Netherlands. It has been found to retain its distinctive characteristics through successive asexual propagations.

DESCRIPTION OF PHOTOGRAPH

This new geranium plant is illustrated by the accompanying photograph which shows blooms, buds, and foliage of the plant; the colors shown are as true as can be reasonably obtained by conventional photographic procedures. The photograph is of a four-month-old plant grown in a lexan-covered greenhouse with normal zonal *pelargonium* culture.

FIG. 1 shows overall plant habit while the inset photograph shows a closer view of the mature inflorescence.

DESCRIPTION OF THE NEW CULTIVAR

The following detailed descriptions set forth the distinctive characteristics of 'Clips Dared'. The data which defines these characteristics were collected from asexual reproductions carried out in Gilroy, Calif. The plant history was taken on seven-month-old plants grown in one-gallon pots in a poly-covered greenhouse during the fall/winter season. The color readings were taken under natural light in the greenhouse in the late winter season. Color references are primarily to The R.H.S. Colour Chart of The Royal Horticultural Society of London (R.H.S.) (2001). Texture description data were collected by viewing plant parts with a dissecting microscope.

DETAILED BOTANICAL DESCRIPTION

Classification:
- *Botanical.*—*Pelargonium×hortorum* L. H. Bailey.
- *Common name.*—Geranium.

Growth:
- *Form.*—Upright, outwardly spreading and rounded growth habit.
- *Growth and branching habit.*—Good vigorous habit, well branched.
- *Height.*—15 cm to 18 cm as measured from soil level to top of plant, excluding blooms; 16 cm to 20 cm soil level to top of umbels.
- *Width.*—30 cm to 40 cm excluding umbels.
- *Time to produce a finished flowering plant.*—8 to 10 weeks.
- *Outdoor plant performance.*—Has good weather tolerance; used in hanging baskets, patio or mixed containers.
- *Time to initiate and develop roots.*—12 to 28 days.
- *Root description.*—White, slightly pubescent, fibrous yet coarse.

Leaves:
- *Arrangement.*—Alternate, simple.
- *Immature leaf.*—Color: Upper surface: RHS 137A. Lower surface: RHS 146B. Length: 3.4 cm to 4.0 cm. Width: 6.5 cm to 8.0 cm.

*Mature leaf.*—Color: Upper surface: RHS 137A. Lower surface: RHS 146B. Length: 4.0 cm to 5.0 cm. Width: 7.0 cm to 8.5 cm.
*Zonation color.*—None.
*Apex description.*—Rounded.
*Base description.*—Cordate.
*Shape.*—Reniform.
*Margin.*—Crenate; somewhat sinuate.
*Texture.*—Pilose, velvety.
*Venation.*—Palmate.
*Venation color.*—RHS 144A.
*Petioles.*—Length: 6.0 cm to 7.0 cm. Diameter: 0.2 cm. Color: RHS 146B. Texture: Pilose; villous.

Stems:
*Length.*—20 cm to 25 cm.
*Internode length.*—0.75 cm to 1.0 cm.
*Color.*—RHS 144B.
*Texture.*—Pilose; villous; few glandular hairs.

Flower buds:
*Length.*—1.2 cm to 1.5 cm.
*Diameter.*—0.6 cm to 0.8 cm.
*Shape.*—Elliptical.
*Color when sepals first divide.*—RHS 45A.

Inflorescence:
*Type.*—An umbel composed of 11 to 15 flowers.
*Umbel diameter.*—8.0 cm to 9.0 cm.
*Umbel depth* (*height*).—6.0 cm to 7.0 cm.
*Blooming habit.*—Continuous blooming throughout the growing season; good floriferousness.
*Peduncle.*—Length: 8 cm to 11 cm. Diameter: 0.3 cm to 0.4 cm. Texture: Pilose; villous; many glandular hairs. Color: RHS 144A.
*Pedicel.*—Length: 2.9 cm to 3.3 cm. Diameter: 0.15 cm. Texture: Many glandular hairs, some with an orange hue. Color: RHS 144A, pigmented by anthocyanin giving it a color of RHS 183A.

Flowers:
*Flower form.*—Polypetalous; mostly imbricate petals and petaloids, semi-double form consisting of 8 to 10 petals and 1 to 2 petaloids.
*Flower diameter.*—5.0 cm to 5.5 cm.
*Flower persistence.*—An open flower will hold its petals until the flower begins to dehisce, 7 to 10 days.
*Fragrance.*—None.

Petals/petaloids:
*Petal size.*—Length: 2.8 cm to 2.9 cm. Width: 2.7 cm to 2.9 cm.
*Shape.*—Obovate.
*Apex.*—Rounded.
*Base.*—Acute.
*Margin.*—Entire.
*Texture.*—Papillose.
*Upper petal color.*—Upper surface: Velvety RHS 45B; basal veining RHS 45A. Lower surface: RHS 46C with streaks of RHS 46A basally.
*Lower petal color.*—Upper surface: Velvety RHS 45B; basal veining RHS 45A. Lower surface: RHS 46C with streaks of RHS 46A basally.
*Upper petaloid color.*—Upper surface: Velvety RHS 45B; basal veining RHS 45A.
*Lower petaloid color.*—Upper surface: Velvety RHS 45B; basal veining RHS 45A.
*Color change with age.*—Colors do not change with age but may change with temperature and time of year.

Sepals:
*Number of sepals.*—5, one larger than the others; fused at base.
*Length of sepals.*—1.0 cm to 1.2 cm.
*Width of sepals.*—0.2 cm to 0.4 cm.
*Shape.*—Linear.
*Apex.*—Acute.
*Texture.*—Villous; many glandular hairs, some with an orange hue.
*Color.*—RHS 143; some anthocyanin in irregular blotches.

Reproductive organs:
*Stamens.*—4 to 6, sometimes fused to petaloids.
*Filament color.*—RHS N155B but whiter with a blush of RHS 54C.
*Filament length.*—0.6 cm.
*Pollen color.*—RHS N30A.
*Pollen amount.*—Moderate.
*Pistil.*—1.
*Pistil length.*—1.0 cm.
*Stigma color.*—RHS 53C.
*Style color.*—RHS 53D.
*Style length.*—0.4 cm.
*Fruit set.*—Not observed.

Disease and insect resistance: Not observed.

Comparison with Known Cultivars

'Clips Dared' differs from the female parent 8691-2 by having darker red flowers, darker green leaves, and a more vigorous growth habit than 8691-2.

'Clips Dared' differs from the comparison variety, 'Rocky Mountain Dark Red' (U.S. Plant Pat. No. 15,513) by having smaller but darker green leaves without a zone.

I claim:

1. A new and distinct cultivar of *Pelargonium* plant as shown and described herein.

* * * * *